United States Patent
Fosaaen et al.

(10) Patent No.: US 10,526,990 B2
(45) Date of Patent: Jan. 7, 2020

(54) SENSING COMBUSTION MISFIRE EVENTS IN ENGINES BY COMPARING SIGNALS DERIVED FROM TWO DIFFERENT TYPES OF OXYGEN SENSORS

(71) Applicant: Kerdea Technologies, Inc., Greenville, NC (US)

(72) Inventors: Ken Ervin Fosaaen, Winterville, NC (US); Horizon Walker Gitano-Briggs, Nibong Tebal (MY)

(73) Assignee: Kerdea Technologies, Inc., Greenville, NC (US)

( * ) Notice: Subject to any disclaimer, the term of this patent is extended or adjusted under 35 U.S.C. 154(b) by 0 days.

(21) Appl. No.: 16/087,696

(22) PCT Filed: Mar. 6, 2018

(86) PCT No.: PCT/US2018/021019
§ 371 (c)(1),
(2) Date: Sep. 24, 2018

(87) PCT Pub. No.: WO2018/165074
PCT Pub. Date: Sep. 13, 2018

(65) Prior Publication Data
US 2019/0293014 A1 Sep. 26, 2019

Related U.S. Application Data

(60) Provisional application No. 62/468,621, filed on Mar. 8, 2017.

(51) Int. Cl.
*G06G 7/70* (2006.01)
*F02D 41/22* (2006.01)
(Continued)

(52) U.S. Cl.
CPC ......... *F02D 41/22* (2013.01); *F02D 41/1441* (2013.01); *F02D 41/1455* (2013.01);
(Continued)

(58) Field of Classification Search
USPC ........................................ 701/114
See application file for complete search history.

(56) References Cited

U.S. PATENT DOCUMENTS 5,996,337 A * 12/1999 Blosser ............... F02D 41/0055
60/274
6,032,653 A * 3/2000 Anamoto ............. F02B 61/045
123/491

(Continued)

FOREIGN PATENT DOCUMENTS

WO 2017155873 A1 9/2017

*Primary Examiner* — Masud Ahmed
(74) *Attorney, Agent, or Firm* — Coats + Bennett, PLLC (57) ABSTRACT

Method and apparatus for monitoring and/or detecting combustion misfire events in periodic combustion processes in internal combustion engines, using combustion signals derived from a first oxygen sensor exposed to exhaust gas of a periodic combustion process and a second oxygen sensor exposed to the same exhaust gas. The first oxygen sensor is resistive-based, and responds relatively faster to changes in the temperature and/or composition of the exhaust gas. The second oxygen sensor is voltaic-based or ampometric-based, and responds relatively slower to changes to the temperature and/or composition of the exhaust gas. When the temperature and/or composition of the exhaust changes rapidly but transiently due to a combustion misfire event, the different response rates of the first and second combustion signals allows for the combustion misfire event(s) to be detected. Either and/or both oxygen sensors may be used to control the engine in a conventional fashion.

20 Claims, 8 Drawing Sheets

(51) Int. Cl.
*F02D 41/14* (2006.01)
*G01M 15/10* (2006.01)
*G01N 27/12* (2006.01)
*G01M 15/11* (2006.01)

(52) U.S. Cl.
CPC .......... *G01M 15/104* (2013.01); *G01M 15/11* (2013.01); *G01N 27/125* (2013.01); *F02D 2200/101* (2013.01); *F02D 2200/1015* (2013.01)

(56) References Cited

U.S. PATENT DOCUMENTS

| | | | |
|---|---|---|---|
| 7,031,828 B1* | 4/2006 | Thompson | F02D 41/1443 123/673 |
| 7,930,147 B2* | 4/2011 | Tuken | G01D 3/02 123/679 |
| 8,586,394 B2 | 11/2013 | Fosaaen | |
| 9,291,526 B2 | 3/2016 | Fosaaen | |
| 9,625,352 B2 | 4/2017 | Fosaaen | |
| 9,784,644 B2* | 10/2017 | Chen | F02D 35/024 |
| 2003/0110845 A1* | 6/2003 | Kumagai | F02D 13/06 73/114.05 |
| 2008/0196485 A1* | 8/2008 | Akimoto | G01M 15/046 73/114.02 |
| 2014/0130588 A1* | 5/2014 | Fosaaen | F02D 41/1446 73/114.72 |
| 2014/0261317 A1* | 9/2014 | Loucks | F02D 41/0087 123/350 |
| 2017/0114766 A1* | 4/2017 | Fujimoto | F02P 3/00 |
| 2017/0159634 A1* | 6/2017 | Fujimoto | F02P 17/00 |

* cited by examiner

SENSING COMBUSTION MISFIRE EVENTS IN ENGINES BY COMPARING SIGNALS DERIVED FROM TWO DIFFERENT TYPES OF OXYGEN SENSORS

RELATED APPLICATIONS

This application claims benefit of U.S. Provisional Application No. 62/468,621, filed 8 Mar. 2017, the disclosure of which is incorporated herein by reference in its entirety.

BACKGROUND

This disclosure relates to a method of monitoring for combustion misfire events in engines or other systems with continual periodic combustion events, and related devices.

In periodic combustion processes, such as those in internal combustion engines, combustion may not take place properly under certain conditions. For example, combustion misfire events occur when the air and fuel mixture is off ratio or improperly mixed and does not combust properly during a given cycle. These misfires may also be due to various electro-mechanical failures such as inadequate firing of the spark plug, malfunctioning fuel injectors, or valve operation anomalies, etc.

Combustion misfires may result in damage to the exhaust management components. Often such phenomena take place intermittently, yet may over time degrade catalyst functionality and/or have a significant impact on the engine and/or emission system performance. Accordingly, it is desirable to detect when combustion misfire events occur in order for corrective measures to be implemented. Currently, pressure sensors located in the compression chamber are used to detect misfire events. However, such pressure sensors are expensive due to the need to design them for the harsh environment of the combustion chambers, and are therefore primarily used for research and high-end vehicles. Combustion misfire events may also be detected by monitoring the angular velocity of the engine's crankshaft for minor variations in the expected rotation of the crankshaft as the result of misfiring; however, this approach requires complex algorithms to deal with the high signal to noise ratio inherent in this approach, and for some applications (e.g., motorcycles) road conditions my create high signal to noise ratio errors, making this approach impractical. Combustion misfire events may also be detected by monitoring analysis of the ionization current in the sparkplug circuit and/or optical measurement of the combustion process, both of which are better suited to basic research than commercial products.

As such, there remains a need for alternative combustion misfire sensors for combustion engines, advantageously one that can be placed outside of the combustion chamber, such as in the exhaust plenum.

SUMMARY

In one or more aspects, the present disclosure is related to sensing combustion misfire events, for example in internal combustion engines, using combustion signals derived from a first oxygen sensor exposed to exhaust gas of a periodic combustion process and a second oxygen sensor exposed to the same exhaust gas (e.g., disposed in the same exhaust plenum of the engine). The first oxygen sensor is resistive-based, and responds relatively faster to changes in the temperature and/or composition of the exhaust gas. The second oxygen sensor is voltaic-based or ampometric-based, and responds relatively slower to changes to the temperature and/or composition of the exhaust gas. Differences in the combustion signals are used to monitor and/or detect combustion misfire events. Either and/or both oxygen sensors may be used to control the engine in a conventional fashion.

In one or more aspects, the present disclosure provides a method of monitoring for a combustion misfire event in an internal combustion engine with continual periodic combustion events. The method comprises generating a first combustion signal; generating a second combustion signal; and monitoring for a combustion misfire event by comparing the first combustion signal and the second combustion signal. The first combustion signal is indicative of an exhaust state of the engine and is based on a time-varying resistance of a first oxygen sensor disposed in an exhaust plenum of the engine. The first oxygen sensor is a resistive based oxygen sensor comprising: a) a metal oxide semiconductor layer bridging a gap between first and second electrodes; and b) a porous protective layer covering the metal oxide semiconductor layer. The second combustion signal is indicative of the exhaust state of the engine based on a second oxygen sensor disposed in the exhaust plenum proximate the first oxygen sensor. The second oxygen sensor is a voltaic-based or ampometric based oxygen sensor. The first oxygen sensor has a first response time for detecting a change in temperature and/or oxygen content of exhaust gases in the exhaust plenum that is at least twice as fast as a second response time of the second oxygen sensor for detecting the same change in temperature and/or oxygen content of exhaust gases in the exhaust plenum.

In some aspects, the monitoring comprises determining that a combustion misfire event has occurred if a difference between the first combustion signal and the second combustion signal exceeds a first threshold. In some aspects, the monitoring comprises determining that a combustion misfire event has occurred if a difference between the first combustion signal and the second combustion signal exceeds a first threshold for at least a minimum duration. In some aspects, the method includes changing the minimum duration in response to a change in speed of the internal combustion engine.

In some aspects, the present disclosure provides a combustion misfire sensor assembly for monitoring for a combustion misfire in an internal combustion engine with continual periodic combustion events. The assembly comprises a first oxygen sensor, a second oxygen sensor, and processing circuitry. The first oxygen sensor is configured to be disposed in an exhaust plenum of the engine. The first oxygen sensor is a resistive based oxygen sensor comprising: a) a metal oxide semiconductor layer bridging a gap between first and second electrodes; and b) a porous protective layer covering the metal oxide semiconductor layer. The second oxygen sensor is configured to be disposed in the exhaust plenum in proximity to the first oxygen sensor. The second oxygen sensor is a voltaic-based or ampometric based oxygen sensor. The processing circuitry is operatively connected to the first and second oxygen sensors and configured to monitor for a combustion misfire by comparing a first combustion signal and a second combustion signal. The first combustion signal is derived from the first oxygen sensor and indicates an exhaust state of the engine based on a time-varying resistance of the first oxygen sensor. The second combustion signal is derived from the second oxygen sensor and indicates the exhaust state of the engine based on a time-varying response of the second oxygen sensor. The first oxygen sensor has a first response time for detecting a change in temperature and/or oxygen content of exhaust gases in the exhaust plenum that is at least twice as fast as a second response time of the second oxygen sensor for detecting the same change in temperature and/or oxygen content of exhaust gases in the exhaust plenum.

In some aspects, the second oxygen sensor is a voltaic-based narrowband oxygen sensor. In some aspects, the second oxygen sensor is an ampometric based wideband oxygen sensor.

In some aspects, the metal oxide semiconductor layer of the first oxygen sensor comprises a p-type metal oxide semiconductor material; in other aspects, the metal oxide semiconductor layer of the first oxygen sensor comprises an n-type metal oxide semiconductor material.

In some aspects, the processing circuitry is configured to determine that a combustion misfire event has occurred if a difference between the first combustion signal and the second combustion signal exceeds a first threshold. In some aspects, the processing circuitry is configured to determine that a combustion misfire event has occurred if the difference between the first combustion signal and the second combustion signal exceeds the first threshold for at least a minimum duration. In some aspects, the processing circuitry is configured to change the minimum duration in response to a change in speed of the combustion engine.

In some aspects, the internal combustion engine is an internal combustion engine for a vehicle.

In some aspects, the first oxygen sensor and the second oxygen sensor are disposed in spaced relation to each other, with the first oxygen sensor disposed operatively upstream of the second oxygen sensor relative to the exhaust plenum. In some aspects, the first and second oxygen sensors are co-located along the exhaust plenum, such as in a hybrid sensor element.

The features, functions and advantages that have been discussed can be achieved independently in various aspects or may be combined in yet other aspects, further details of which can be seen with reference to the following description and the drawings.

DESCRIPTION

In one or more aspects, the present disclosure is generally related to monitoring and/or detecting combustion misfire events in periodic combustion processes in internal combustion engines, using combustion signals derived from a first oxygen sensor exposed to exhaust gas of a periodic combustion process and a second oxygen sensor exposed to the same exhaust gas (e.g., disposed in the same exhaust plenum of the engine). The first oxygen sensor is resistive-based, and responds relatively faster to changes in the temperature and/or composition of the exhaust gas. The second oxygen sensor is voltaic-based or ampometric-based, and responds relatively slower to changes to the temperature and/or composition of the exhaust gas. When the temperature and/or composition of the exhaust changes rapidly but transiently due to a combustion misfire event, the different response rates of the first and second combustion signals allows for the combustion misfire event(s) to be detected. In addition, either and/or both oxygen sensors may be used to control the engine in a conventional fashion.

For simplicity, the discussion herein may generally be in the context of a small displacement gasoline powered spark ignition internal combustion engine, but it should be understood that the methods and devices disclosed herein may be used in other periodic internal combustion engine applications, such as compression ignition engines, hydrogen powered engines, other hydrocarbon powered engines, diesel engines, Homogeneous Charge Compression Ignition (HCCI) engines, and Reactivity Controlled Compression Ignition (RCCI) engines, etc. These internal combustion engines may be used for any suitable purpose, such as for vehicles (automobiles, motorcycles, boats, generators, trains, ships, etc.), or for generating electrical power in a static location, or for providing mechanical power to non-vehicle equipment. The relevant internal combustion engines utilize a periodic combustion process (with "cycles"), but the period between the combustion events is variable based on the speed (i.e., rpm) of the engine 10.

Figure 1:
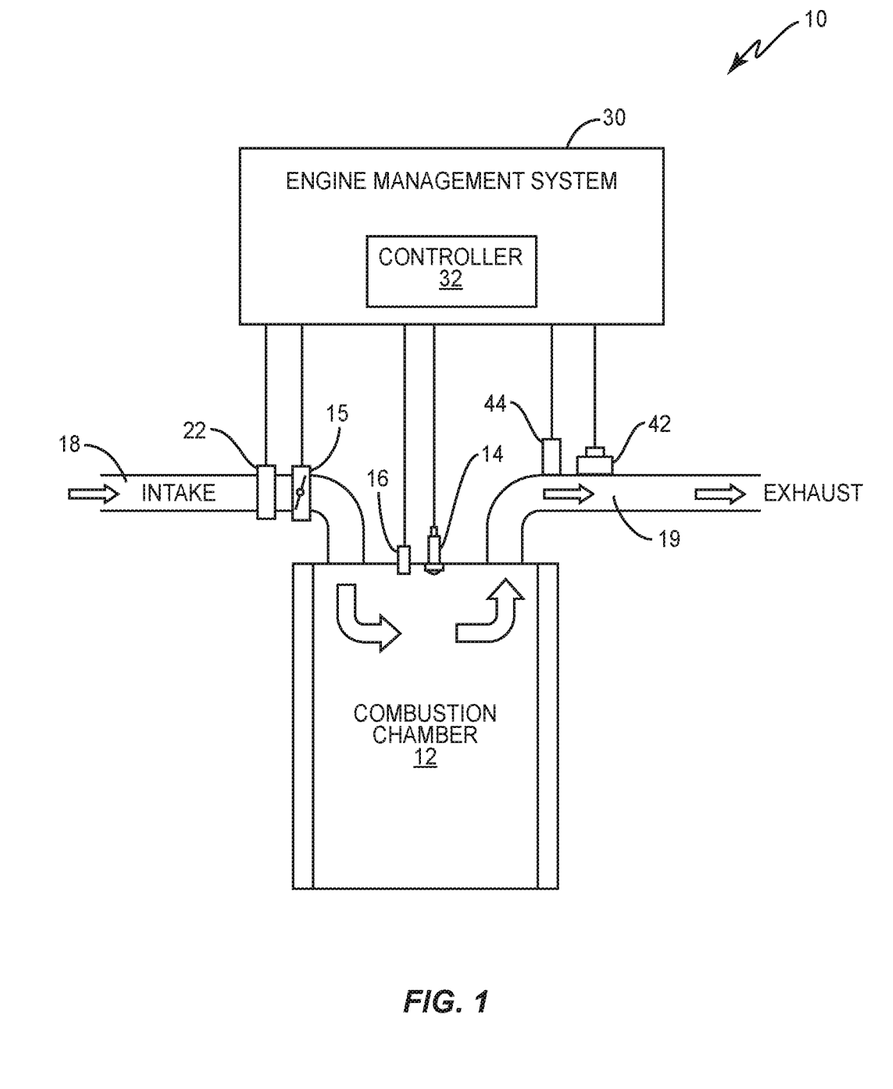
FIG. 1 shows schematic representation of an engine, having an oxygen sensor based combustion sensor assembly of one or more aspects and/or where the method of the one or more aspects may be implemented.

FIG. 1 shows a schematic of an exemplary internal combustion engine 10, with continual periodic combustion events, which may be of any type (e.g., piston, rotary, nutating disk, etc.). The engine 10 includes at least one combustion chamber 12 with associated piston, valves, etc. (not shown), an intake manifold 18, an exhaust plenum 19, and an engine management system 30. The intake manifold 18 supplies air to the combustion chamber 12. A mass airflow (MAF) sensor or manifold air pressure (MAP) sensor 22, advantageously with associated air intake temperature sensor, is shown as disposed in the intake manifold 18 so that the incoming air conditions may be monitored as the airflow changes due to the opening or closing of the throttle body 15 which is monitored and used to control the load/speed of the engine, typically based on operator demand. A controllable fuel metering system, such as a fuel injector 16, supplies fuel to the combustion chamber under control of the engine management system 30. For diesel engines, the fuel injector 16 typically sprays fuel directly into the combustion chamber 12, and ignition takes place as a result of reaching a particular compression level. For spark ignition engines, the fuel injector 16 may spray fuel into the intake manifold or directly into the combustion chamber 12, and a spark ignition device 14 (e.g., spark plug) operates under the control of the engine management system 30 to ignite the air and fuel mixture in the combustion chamber 12 at the desired time in the cycle for proper combustion. The first oxygen sensor 42 and the second oxygen sensor 44 are both disposed in the exhaust plenum 19. The engine management system 30 includes one or more processing circuits 32 (collectively "controller") that control the fuel supply amount and timing, ignition timing, and other engine parameters based on the input from the various sensors and the programming of the processing circuits 32. For example, the engine management system 30 uses the oxygen sensors 42,44, as described herein, to help monitor for engine misfire events. In some aspects, the engine management system 30 also uses either and/or both first and second oxygen sensors 42,44 to control the engine 10 in a conventional fashion, in addition to providing the combustion misfire functionality. Other than some particulars of the oxygen sensors 42, 44 and operation of the processing circuit(s) 32 described in greater detail herein, the configuration and operations of the engine 10 are well known to those of skill in the art, and are not discussed further herein in the interests of clarity.

Figure 9:
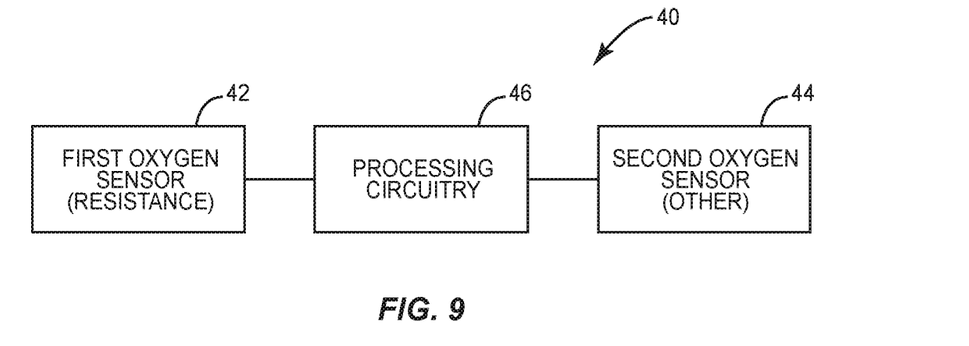
FIG. 9 shows a simplified schematic of a combustion misfire sensor assembly of one or more aspects.

A combustion misfire sensor assembly 40, shown in FIG. 9, is associated with the engine 10, and configured to monitor monitoring for combustion misfires in the engine 10. Referring to FIG. 9, the combustion misfire sensor assembly 40 comprises the first oxygen sensor 42, the second oxygen sensor 44, and suitable processing circuitry 46. As discussed further below, the first oxygen sensor 42 is configured to be disposed in the exhaust plenum 19 of the engine 10, and the first oxygen sensor 42 is a resistive-based oxygen sensor. The second oxygen sensor 44 is also configured to be disposed in the exhaust plenum 19, in proximity to the first oxygen sensor 42, and the second oxygen sensor 44 is a voltaic-based or ampometric-based oxygen sensor. The processing circuitry 46 is operatively connected to the first and second oxygen sensors 42,44.

The first oxygen sensor 42 is a resistive-based oxygen sensor that includes a metal oxide semiconductor (MOS) layer 54 bridging a gap between first and second electrodes 52,53 and covered by a porous protective layer 55. Resistive-based oxygen sensors generally operate by exploiting the variable resistance of metal oxide semiconductor materials when exposed to variable level of oxygen at typical engine exhaust temperatures. Examples of resistive-based oxygen sensors are described in U.S. Pat. Nos. 8,586,394 and 9,625,352. In general, resistive-based oxygen sensors are very fast in their response to changes in the temperature and/or oxygen content of the exhaust environment to which they are exposed. In some aspects, the first oxygen sensor 42 is of a single MOS type (either an n-type or p-type MOS, but not both) that measures best in either the rich region or the lean region, but not both, such as described in U.S. Pat. No. 8,586,394. In some aspects, the first oxygen sensor 42 is a dual MOS type (both an n-type and a p-type MOS), such as that described in U.S. Pat. No. 9,625,352. In general, assuming a constant voltage is supplied to the first oxygen sensor 42, the resistance of the MOS semiconductor layer that bridges the gap between the relevant electrodes (and hence the voltage drop across the oxygen sensor) should vary with the temperature of the exhaust in the exhaust plenum 19, and with the oxygen content of the exhaust. As discussed herein, the time-varying resistance of the first oxygen sensor 42 while the engine 10 is running may be used to monitor for combustion misfire events, in combination with the information from the second oxygen sensor 44.

Figure 2:
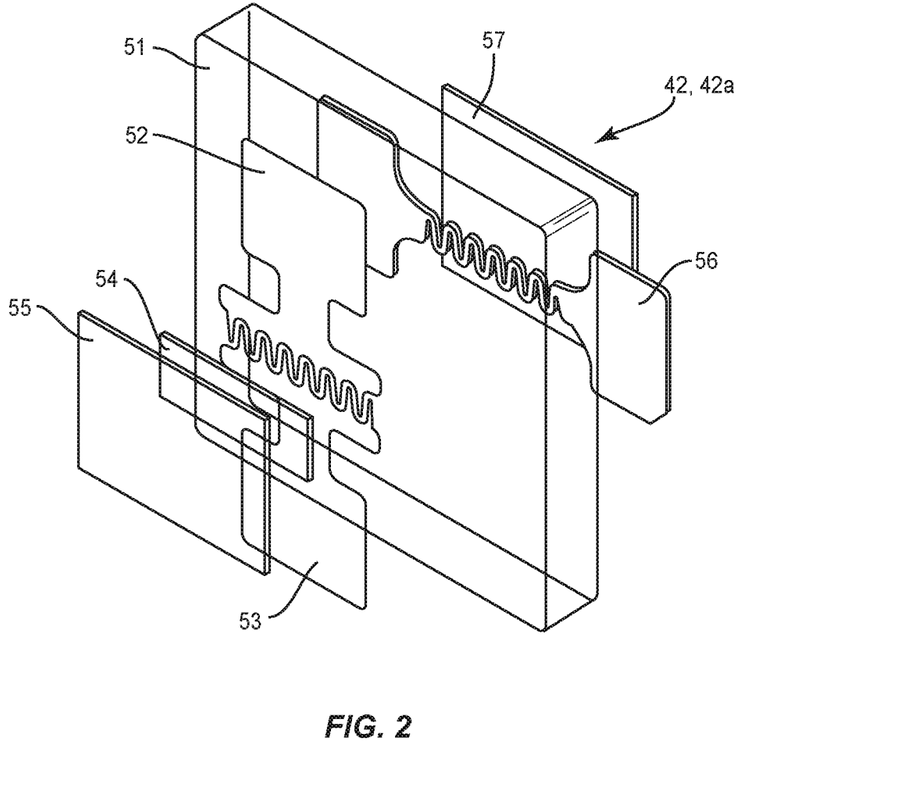
FIG. 2 shows an exploded view of a resistive-based oxygen sensor of one or more aspects.
Figure 3:
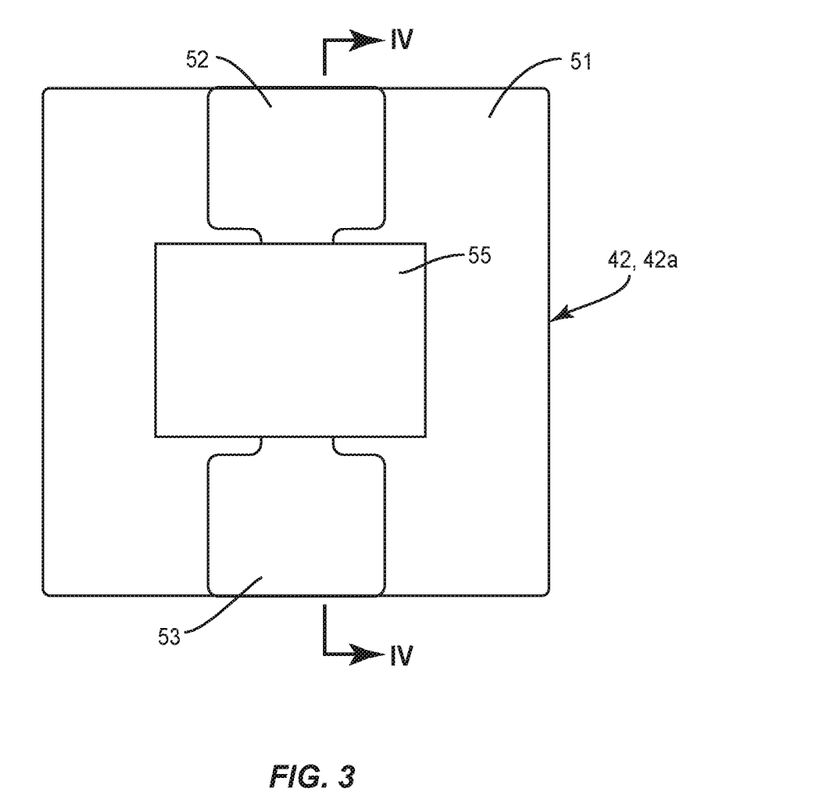
FIG. 3 shows a top view of the resistive-based oxygen sensor of FIG. 2.
Figure 4:
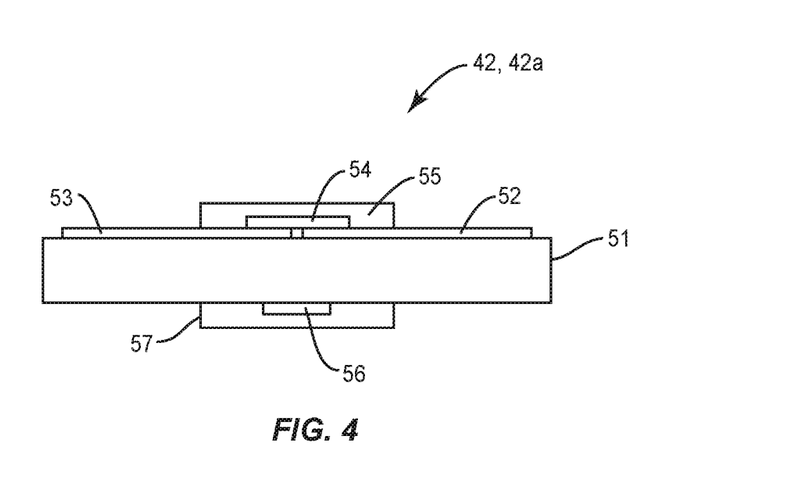
FIG. 4 shows a simplified cross-section view of the resistive-based oxygen sensor of FIG. 3 along line IV-IV.

Referring to FIGS. 2-4, first oxygen sensor 42 is shown as a single MOS type oxygen sensor 42a. The first oxygen sensor 42a of FIGS. 2-4 includes a metal oxide semiconductor (MOS) layer 54 bridging a gap between first and second electrodes 52, 53 and covered by a porous protective layer 55. The first and second electrodes 52,53 are disposed on a substrate 51 in spaced relation to each other, so that the gap is present between the first and second electrodes 52,53. The MOS layer 54 is physically disposed over the gap and at least part of the first and second electrodes 52,53, and forms a semiconductor bridge between the first and second electrodes 52,53. The porous protective layer 55 is disposed over the MOS layer 54, and may contain catalytic materials to enhance performance. The resistance of the MOS layer 54 changes with temperature and oxygen content of exhaust gas to which the oxygen sensor 42 is exposed, and is dependent upon the nature of the semiconductor used. An n-type semiconductor increases in resistance when exposed to more oxygen, and a p-type semiconductor decreases in resistance when exposed to more oxygen. For the oxygen sensor of FIGS. 2-4, the MOS layer 54 comprises either an n-type metal oxide semiconductor material or a p-type metal oxide semiconductor material. In some aspects, the first oxygen sensor 42 optionally includes a heater element 56 mounted to the substrate 51 opposite the first and second electrodes 52,53, with the heater element 56 covered by an electrically insulating layer 57. Attention is directed to U.S. Pat. No. 8,586,394 for further details of other arrangements of single MOS type oxygen sensors, including ones where the heater element 56 is located between the first and second electrodes 52,53 and the substrate 51.

Figure 5:
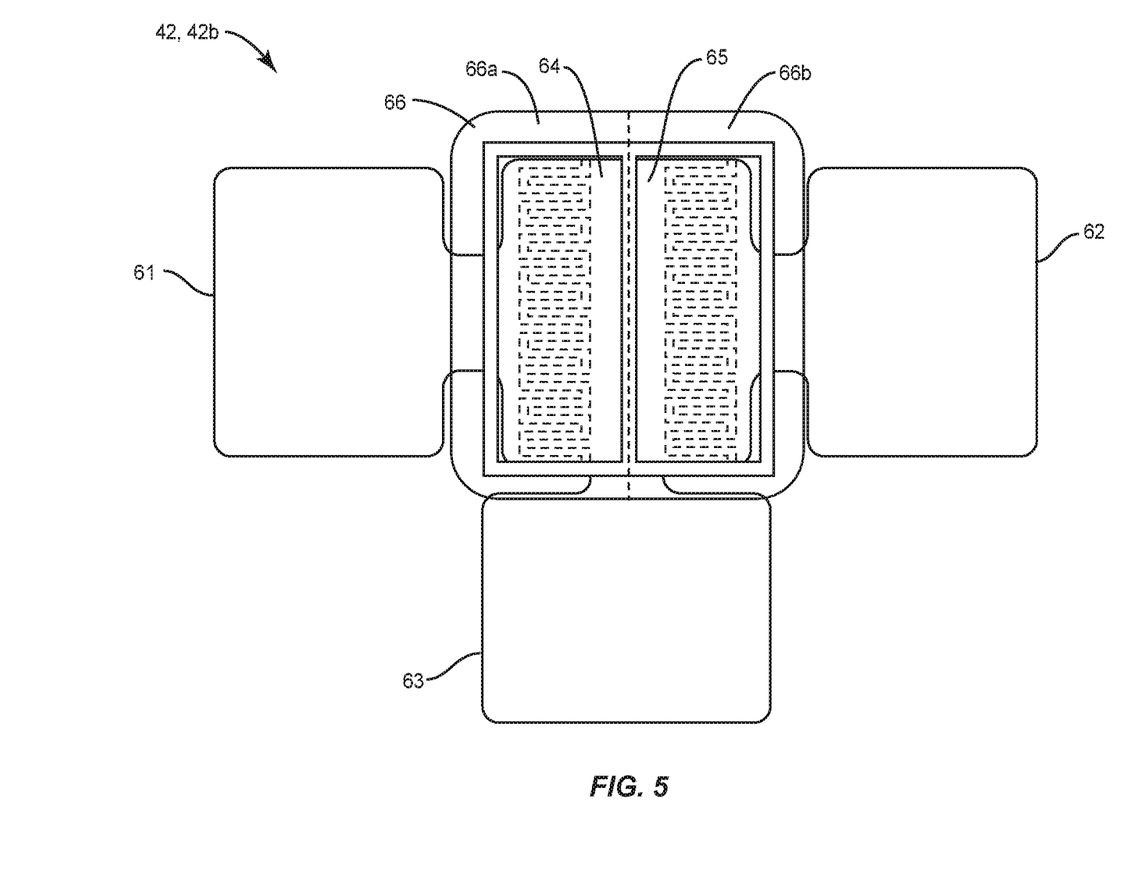
FIG. 5 shows a top view of a dual metal oxide semiconductor (dual MOS) resistive-based oxygen sensor of one or more aspects.

As mentioned above, in some aspects, the first oxygen sensor 42 is a dual MOS type (both an n-type and a p-type MOS), such as that described in U.S. Pat. No. 9,625,352. First oxygen sensor 42 is shown in FIG. 5 as a dual MOS type oxygen sensor 42b. The first oxygen sensor 42b of FIG. 5 includes first and second sensing electrodes 61,62, which functionally correspond to the first electrode 52 in FIG. 2, are disposed in spaced relationship to a common electrode 63, which functionally corresponds to the second electrode 53 of FIG. 2, with gaps defined therebetween. An n-type semiconducting layer 64 (comprising an n-type MOS material) is disposed over the gap between the first sensing electrode 61 and the common electrode 63, and forms a semiconductor bridge between the first sensing electrode 61 and the common electrode 63. A p-type semiconducting layer 65 (comprising a p-type metal oxide semiconducting material) is disposed over the gap between the second sensing electrode 62 and the common electrode 63, and forms a semiconductor bridge between the second sensing electrode 62 and the common electrode 63. Porous dielectric protective coating layer 66 may be placed over the MOS layers 64,65 and neighboring portions of the electrodes. This protective coating layer 66 may be on continuous coating layer over both MOS layers 64,65, with respective first and second portions, or the first portion 66a and second portion 66b may be distinct and spaced from each other. The protective layer 66, in some aspects, contains catalytic materials to enhance performance. The dual MOS type oxygen sensor 42b, in some aspects, includes a heater portion (not shown). Note that with a dual MOS type oxygen sensor, the n-type MOS portion can be monitored for misfires in the rich exhaust gas region, and the p-type MOS portion can be used to monitor for misfires in the lean region, as described further below. Attention is directed to U.S. Pat. No. 9,635,352 for further details of other arrangements of dual MOS type oxygen sensors.

Note that reference number 42 is used to refer to the first oxygen sensor when it does not matter whether the first oxygen sensor 42 is of a single MOS type (e.g., oxygen sensor 42*a*) or of a dual MOS type (e.g., oxygen sensor 42*b*).

The second oxygen sensor 44 may be a conventional voltaic-based oxygen sensor known in the art, or may be conventional ampometric-based oxygen sensor known in the art. Thus, in some aspects, the second oxygen sensor 44 is a voltaic-based oxygen sensor, sometimes referred to as a narrowband sensor; in other aspects, the second oxygen sensor 44 is an ampometric-based oxygen sensor, sometimes referred to as a wideband sensor.

A voltaic-based, or narrowband, oxygen sensor generates a voltage signal based upon an electromotive force (EMF) developed across an oxygen ion ($O^{2+}$) conducting material (typically partially stabilized zirconia) separating the exhaust atmosphere from a reference atmosphere (ambient air) according to the well-known Nernst equation:

$$\text{emf} = \frac{RT}{zF}\ln\left(\frac{P'O2}{P''O2}\right)$$

Where R is the universal gas constant, T is temperature in degrees K, F is the Faraday constant, and $$\left(\frac{P'O2}{P''O2}\right)$$

is the ratio of oxygen partial pressures for the two atmospheres (exhaust and reference air). When the engine is operating in a fuel rich state (more fuel than required at stoichiometry), the oxygen difference is very high, and a high EMF signal is generated due to the high chemical potential across the ion conductor. When the engine is operating in a fuel lean state (less fuel than required at stoichiometry, $\lambda<1$), the oxygen difference is significantly lower, and a lower EMF signal is generated due to the reduced chemical potential across the ion conductor. Note that the response time for voltaic-based oxygen sensors are slow relative to the intermittent combustion misfiring taking place in the engine.

An ampometric-based, or wideband, oxygen sensor generates a pumping current that seeks to keep a voltaic oxygen sensor circuit on the same element at $\lambda=1.00$, and therefore changes based upon changes in the oxygen content in the exhaust. In rich conditions, oxygen is pumped in an associated pumping chamber, and in lean conditions, oxygen is pumped out of the pumping chamber. This pumping current is typically converted to a voltage signal in any conventional manner. There is second type of wideband sensor currently being used in the automobile industry, with a different structure and operating principles, but it also operates based upon a pumping current that is dependent upon the oxygen content in the exhaust gas being monitored, and is able to provide quantitative values for oxygen in the exhaust gas to which it is exposed. The response time for ampometric oxygen sensors is slow relative to the intermittent combustion misfiring taking place in the engine.

As mentioned above, resistive-based oxygen sensors are very fast in their response to changes in the temperature and/or oxygen composition of the exhaust to which they are exposed. In contrast, both the voltaic-based and ampometric-based oxygen sensors are relatively slower to respond to changes in the temperature and/or oxygen composition of the exhaust to which they are exposed. Indeed, the resistive-based oxygen sensors are at least twice as fast to respond to changes in the temperature and/or oxygen composition of the exhaust to which they are exposed. Thus, in many situations where the first and second oxygen sensors 42,44 are exposed to the same exhaust stream, the first oxygen sensor 42 will respond to a single combustion misfire event, while the second oxygen sensor 44 will not significantly respond. Therefore, a comparison of combustion signals derived from the two different type of oxygen sensors 42,44 can be used to monitor and/or detect combustion misfire events.

It should be noted that the first oxygen sensor 42 is shown in FIG. 1 as being disposed downstream of the second oxygen sensor 44, relative to the flow through the exhaust plenum 19. However, in some aspects, this sequence is reversed, and second oxygen sensor 44 is disposed downstream of the first oxygen sensor 42, relative to the flow through the exhaust plenum 19. In some aspects, the first and second oxygen sensors 42,44 are disposed neither upstream nor downstream of each other relative to the flow through the exhaust plenum 19, but are instead disposed at a same flow distance along the exhaust plenum 19, optionally at different peripheral locations on the exhaust plenum 19. In some aspects, the first and second oxygen sensors 42,44 are co-located along the exhaust plenum 19, such as in a combined "hybrid" package, discussed further below. Further, it should be noted that the sensitivity of the first oxygen sensor 42 to combustion misfire events is determined by sensor design as well as the accompanying circuit design.

Figure 6:
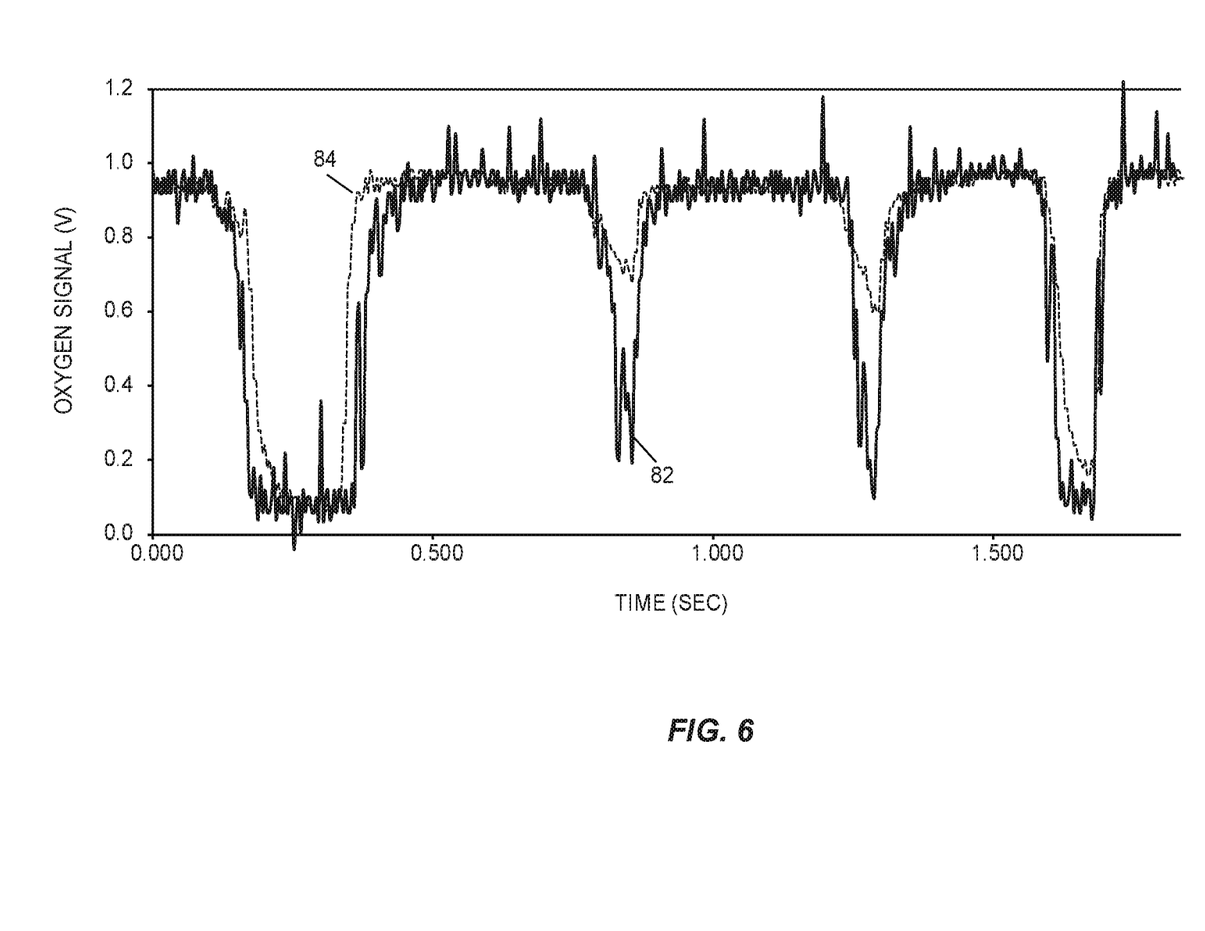
FIG. 6 shows exemplary first and second combustion signals over time, when the engine is running in a rich region and running in a lean region, with no combustion misfires.

The processing circuitry 46 is operatively connected to the first and second oxygen sensors 42,44 and configured to monitor for a combustion misfire by comparing a first combustion signal 82 and a second combustion signal 84. Exemplary first combustion signal 82 and second combustion signal 84 are shown in FIG. 6. The first combustion signal 82 is derived from the first oxygen sensor 42 and indicates an exhaust state of the engine 10 based on a time-varying resistance of the first oxygen sensor 42. The second combustion signal 84 is derived from the second oxygen sensor 44 and indicates the exhaust state of the engine 10 based on a time-varying response of the second oxygen sensor 44. The first oxygen sensor 42 has a first response time for detecting a change in temperature and/or oxygen content of exhaust gases in the exhaust plenum 19 that is at least twice as fast as a second response time of the second oxygen sensor 44 for detecting the same change in temperature and/or oxygen content of exhaust gases in the exhaust plenum 19.

The processing circuitry 46 may be a dedicated circuit, or may be a portion of a more general purpose circuit. Thus, in some aspects, controller 32 serves as the processing circuitry 46 of the combustion misfire sensor assembly in addition to any other suitable functions. In some aspects, a dedicated processor may serve as the processing circuitry 46 of the combustion misfire sensor assembly, advantageously supplying suitable information about detected combustion misfire events to the engine management system 30.

If the engine 10 is operating properly without combustion misfire events, the first combustion signal 82 (derived from first oxygen sensor 42) and the second combustion signal 84 (derived from the second oxygen sensor 44) will follow roughly the same pattern, or a known relative pattern. See FIG. 6, where the first and second combustion signals 82,84 follow a similar path, particularly when the change in exhaust gas temperature and/or composition is relatively long in duration. Note that in FIG. 6, the engine is initially running in the rich region (air:fuel ratio, represented by $\lambda$, less than 1.0), then switches to the lean region ($\lambda$ greater than 1.0), and then back to the rich region, and then to the lean region, and so forth, and that first oxygen sensor 42 used to generate the first combustion signal 82 is using an n-type semiconductor as the relevant MOS layer 54,64. Note further that in FIG. 6, no combustion misfire events are present, and the very short duration spikes present in the first combustion signal 82 are the result of noise, such as spark induced noise.

When a combustion misfire event takes place, the exhaust gasses expelled from the combustion chamber 12 have not significantly reacted, and as such, it is slightly cooler and there is an excess of free oxygen in the exhaust gases passing both the first and second oxygen sensors 42,44. As discussed above, the first oxygen sensor 42 responds significantly faster than the second oxygen sensor 44. As such, the first oxygen sensor 42 responds to a quick combustion misfire event, whereas the second oxygen sensor 44 may not register a significant change unless the combustion misfire event repeats successively for a longer period of time. See FIG. 7, where the first combustion signal 82 derived from first oxygen sensor 42 drops whenever a combustion misfire event takes place, but the second combustion signal 84 derived from the second oxygen sensor 44 does not respond fast enough to register the change in exhaust state before the combustion continues on in subsequent cycles.

With the above in mind, the processing circuitry 46, in some aspects, determines that a combustion misfire event has occurred if a difference between the first combustion signal 82 and the second combustion signal 84 exceeds a first threshold. In some aspects, the first threshold is fixed; in some aspects, the first threshold may be varied, such as by the engine management system 30. In some aspects, the processing circuitry 46 determines that a combustion misfire event has occurred if the difference between the first combustion signal 82 and the second combustion signal 84 exceeds the first threshold for at least a minimum duration. In some aspects, the minimum duration is fixed; in some aspects, the minimum duration is variable, such as being set/adjusted by the processing circuitry 46 based on the speed of the engine 10, or in response to a change in speed of the engine 10.

Figure 8:
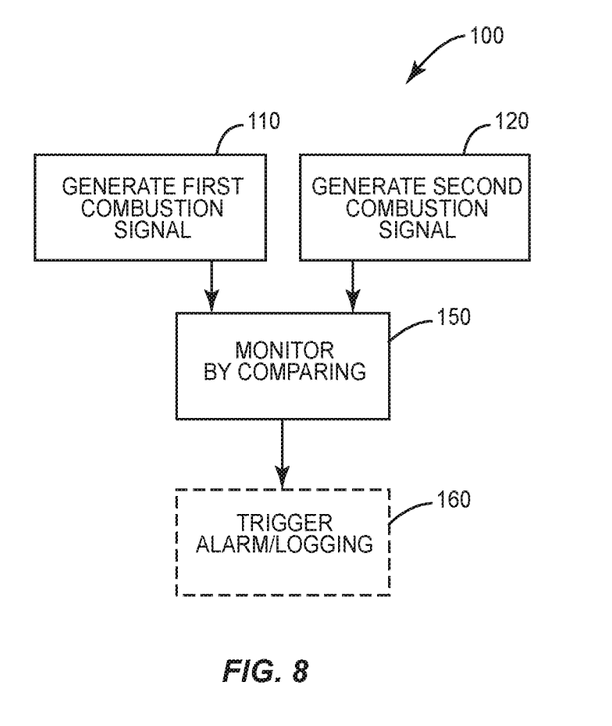
FIG. 8 shows simplified flowchart of a method of monitoring for a combustion misfire, according to one or more aspects.

In one or more aspects, the present disclosure is directed to a method (100) of monitoring for a combustion misfire in an internal combustion engine 10 with continual periodic combustion events. The method comprises generating (110) a first combustion signal 82 and generating (120) a second combustion signal 84. Note that in some aspects, step 110 is performed before step 120; in some aspects, step 110 is performed after step 120; in some aspects, step 110 and 120 overlap each other and/or are concurrent. The first combustion signal 82 is indicative of an exhaust state of the engine 10 based on the time-varying resistance of the first oxygen sensor 42 (which is disposed in the exhaust plenum 19 of the engine 10). As mentioned above, the first oxygen sensor 42 is a resistive-based oxygen sensor comprising a metal oxide semiconductor layer 54 or 64 or 65 bridging a gap between first and second electrodes 52,53 or 61,63 or 62, 63, and covered by a porous protective layer 55,66 covering the metal oxide semiconductor layer. The second combustion signal 84 is also indicative of the exhaust state of the engine 10, but is based on the response of the second oxygen sensor 44 (also disposed in the exhaust plenum 19, proximate the first oxygen sensor 42). The second oxygen sensor 44 is a voltaic-based or ampometric based oxygen sensor. As discussed above, the first oxygen sensor 42 has a first response time for detecting a change in temperature and/or oxygen content of exhaust gases in the exhaust plenum 19 that is at least twice as fast as a second response time of the second oxygen sensor 44 for detecting the same change in temperature and/or oxygen content of exhaust gases in the exhaust plenum 19. The process includes monitoring (150) for a combustion misfire by comparing the first combustion signal 82 and the second combustion signal 84.

The comparison of the first and second combustion signals 82,84 may find that the first and second combustion signals 82,84 track each other well, and thus the monitoring for a combustion misfire event will indicate that no combustion misfire events have occurred. Alternatively, the comparison of the first and second combustion signals 82,84 may find that the first and second combustion signals 82,84 do not track each other well for a short duration, indicating that a combustion misfire event has occurred. For example, the comparison of the first and second combustion signals 82,84 may find that the first and second combustion signals 82,84 differ by more than a first threshold. If so, then a combustion misfire event is indicated. Thus, the monitoring (150) comprises, in some aspects, determining that a combustion misfire event has occurred if a difference between the first combustion signal 82 and the second combustion signal 84 exceeds a first threshold. In some aspects, the monitoring (150) comprises determining that a combustion misfire event has occurred if a difference between the first combustion signal 82 and the second combustion signal 84 exceeds a first threshold for at least a minimum duration. The indication of a combustion misfire causes, in some aspects, triggering (160) of a corresponding appropriate alarm and/or logging of the combustion misfire event.

The first and second combustion signals 82,84 may be derived from their respective oxygen sensors in any suitable way. For example, the resistance across the first oxygen sensor 42 may be measured via a suitable voltage divider network, and that resistance converted to a string of values. Likewise, the EMF values from the second oxygen sensor 44 can be measured via a suitable circuit and converted to a string of values. Both the first combustion signal 82 and/or the second combustion signal 84 may be smoothed or otherwise processed using known signal processing techniques to remove noise (such as noise induced by spark events), prior to the comparison.

Figure 7:
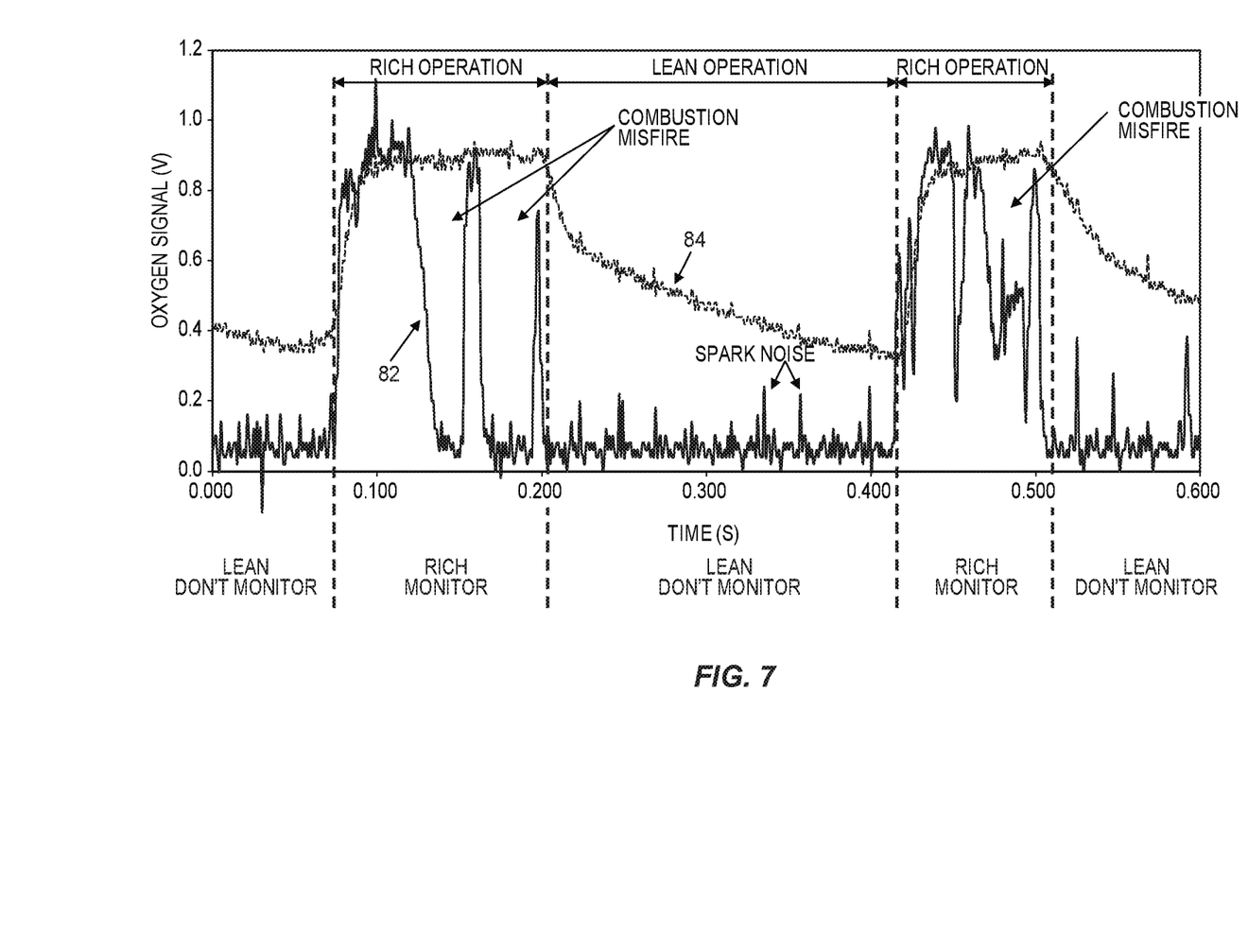
FIG. 7 shows exemplary first and second combustion signals over time, when the engine is running in a rich region and running in a lean region, with some combustion misfires.

In some aspects, the MOS layer of the first oxygen sensor 42 is a n-type semiconductor and the second oxygen sensor 44 is a narrowband zirconia sensor. With this configuration, the engine management system 30 causes the engine 10 to operate alternatively rich and lean. If combustion misfire events take place, they will typically do so in both the rich and lean regions, therefore the processing circuitry 46 may focus on the responses in the rich region and ignore the lean region for detection of combustion misfire events. When the engine 10 is operating in the rich region, the processing circuitry 46 monitors the first and second combustion signals 82,84 and compares them, as discussed above. If both the first combustion signal 82 (derived from the first oxygen sensor 42) and the second combustion signal 84 (derived from the second oxygen sensor 44) indicate rich operation, then the processing circuitry 46 determines that no combustion misfire event has taken place. If, however, a combustion misfire event takes place, the exhaust will have an excess of free oxygen and the first combustion signal 82 will change accordingly for one or a few cycles indicating a lean condition, whereas the second combustion signal 84 will continue to indicate a rich condition. Thus, the difference between the first combustion signal 82 and the second combustion signal 84 will be large, with the second combustion signal 84 being larger than the first combustion signal 82. When the difference is larger than a threshold, the presence of a combustion misfire event is indicated. As an example, the processing circuitry 46 may consider a signal below 450 mV to be lean and above 450 mV to be rich. Using a suitable circuit, e.g., a voltage divider circuit, to derive the first combustion signal 82 from the time-varying resistance of the first oxygen sensor 42 so as to be readily comparable to the second combustion signal 84 derived from the second oxygen sensor 44 (zirconia sensor in this example), and using the example of FIG. 7, the first combustion signal 82 drops below 450 mV (close to 0.00 mV) then returns to above 450 mV. In the example of FIG. 7, this occurs twice in the time period of about 0.085 seconds to about 0.2 seconds, when the engine management system 30 is calling for rich operation. Thus, two combustion misfire events are detected in that time period.

In some aspects, the MOS layer of the first oxygen sensor 42 is a p-type semiconductor and the second oxygen sensor 44 is a narrowband zirconia sensor. With this configuration, the engine management system 30 causes the engine 10 to operate alternatively rich and lean, like described immediately above. However, in this configuration it is appropriate for the processing circuitry 46 to focus on the first combustion signal 82 during the operation in the lean region, and ignore the rich region portion. Thus, when the engine 10 is operating in the lean region, the processing circuitry 46 monitors the first and second combustion signals 82,84 and compares them. If both the first combustion signal 82 (derived from the first oxygen sensor 42) and the second combustion signal 84 (derived from the second oxygen sensor 44) indicate lean operation, then the processing circuitry determines that no combustion misfire event has taken place. If, however, a combustion misfire event takes place, the first combustion signal 82 will change accordingly for one or a few cycles indicating a rich condition, whereas the second combustion signal 84 will continue to indicate a lean condition. Thus, the difference between the first combustion signal 82 and the second combustion signal 84 will be large, with the second combustion signal 84 being less than the first combustion signal 82. When the difference is larger than a threshold, the presence of a combustion misfire event is indicated.

When the first oxygen sensor 42 is a dual MOS sensor system (both n-type and p-type MOS on the same resistive sensor) and the second oxygen sensor 44 is a narrowband zirconia sensor, the processing circuitry 46 looks at the responses of both portions of the first oxygen sensor 42 simultaneously or separately during both the rich and lean operation regions to determine if a combustion misfire event takes place. The dual MOS oxygen sensor 42b could be monitored with separate circuit loops for the n-type semiconductor portion (or sub-circuit) and the p-type semiconductor portion (or sub-circuit), or in the same circuit by running them in parallel or series. The relevant first combustion signal 82 would be compared to the second combustion signal 84 (derived from the second oxygen sensor 44), as described above.

In some aspects, signal processing may be used to lessen the impact of potential signal noise from spark noise. Spikes in the first combustion signal 82 may occur due to extraneous signals (from spark plugs, for example) and may not be due to combustion misfire events. Thus, in some aspects, the processing circuitry 46 looks for a signal anomaly (the difference between the first and second combustion signals 82,84) indicating a combustion misfire event to occur for a threshold amount of time, and discount/ignore anomalies that occur for shorter periods of time. For instance, assume the engine used in the example of FIG. 7 was operating at 3000 rpm, and would therefore experience a cycle every 0.020 seconds (20 ms), and a combustion event every 40 ms. In the example of FIG. 7, several spark induced spikes can be seen on the base curve that last about five milliseconds. To rule out "signal noise," a minimum duration for the unexpected lean condition signal from the first oxygen sensor 42 could be set to a longer time than one would expect from noise, and that value could depend on the engine speed. In this example, twenty milliseconds would be practical. At higher rpm's the threshold time would be reduced; at lower rpms, the threshold time could be increased.

The discussion above has been generally in the context of an engine 10 having a single combustion chamber 12, for better clarity. However, the present invention is not limited to single combustion chamber engines, and may be used with multiple combustion chamber (multiple cylinder) engines as well. And, a single combustion sensor pair 42,44 or combustion misfire sensor assembly 40 may cover multiple combustion chambers 12, or there may be a dedicated combustion sensor pair 42,44 and/or combustion misfire sensor assembly 40 for each combustion chamber 12 of the engine 10. In some versions, a single controller 32 may take and process data from several oxygen sensors 42,44 acting as combustion sensors. Further, it should be noted that placement of the oxygen sensors 42,44 further upstream in the exhaust plenum 19 is believed to improve performance. Thus, it may be advantageous to "close couple" oxygen sensor(s) 42,44 to the combustion chamber(s) 12. Also, it should be noted that, in some aspects, the time-varying resistance of the oxygen sensors 42,44 is determined by observing changes in voltage or current through the oxygen sensor 42,44, and be represented by a varying voltage, or a varying current, or digital values, or any other known approach to representing time-varying values.

Figure 10:
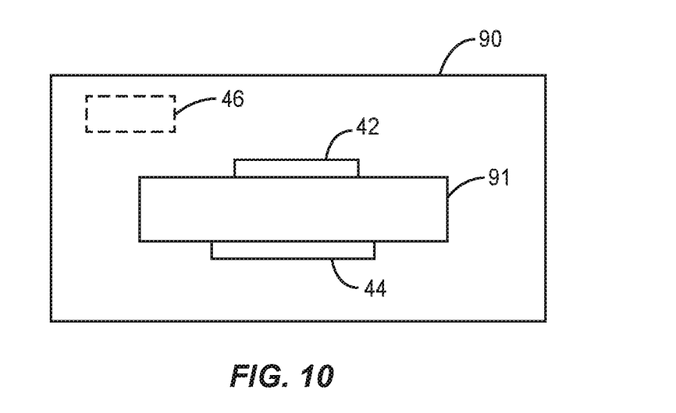
FIG. 10 shows a simplified cross-section of a hybrid sensor package according to one or more aspects.

The discussion above has generally been in the context of the second oxygen sensor 44 being closely located to the first oxygen sensor 42, but spaced therefrom along the exhaust plenum 19. However, as pointed out above, in some aspects, the first and second oxygen sensors 42,44 are co-located along the exhaust plenum 19. In some aspects the first and second oxygen sensors 42,44 are provided in a common mounting package to form a hybrid sensor package 90. See FIG. 10. The hybrid sensor package 90 includes a first oxygen sensor 42, which is a resistive-based oxygen sensor comprising a metal oxide semiconductor layer 54 or 64 or 65 bridging a gap between first and second electrodes 52,53 or 61,63 or 62,63, and covered by a porous protective layer 55,66 covering the metal oxide semiconductor layer. The hybrid sensor package 90 also includes a second oxygen sensor 44, which is a voltaic-based or ampometric based oxygen sensor. As discussed above, the first oxygen sensor 42 has a first response time for detecting a change in temperature and/or oxygen content of exhaust gases in the exhaust plenum 19 that is at least twice as fast as a second response time of the second oxygen sensor 44 for detecting the same change in temperature and/or oxygen content of exhaust gases in the exhaust plenum 19. In some aspects, the first and second oxygen sensors 42,44 of the hybrid sensor package 90 are disposed on opposite sides of a suitable substrate 91; in some aspects, the first and second oxygen sensors 42,44 of the hybrid sensor package 90 are disposed on the same side of the substrate 91. Regardless of which side of the substrate 91 that the second oxygen sensor 44 is disposed on, a portion of the second oxygen sensor 44 may extend into the substrate 91, if appropriate to achieve a compact structure. In some aspects, the hybrid sensor package includes processing circuitry 46; in some aspects, the processing circuitry 46 is external to the hybrid sensor package 90 so that the hybrid sensor package 90 is conceptually a two element oxygen sensor element. The first and second oxygen sensors 42,44 of the hybrid sensor package 90 have independent data leads so that the signals from the first and second oxygen sensors 42,44 of the hybrid sensor package 90 can be provided to the processing circuitry 46 so as to derive the first and second combustion signals 82, 84. The hybrid sensor package 90 is designed to be installed in the exhaust plenum 19, to provide the first and second oxygen sensors 42,44 in a convenient fashion.

The methods and engine control apparatuses discussed above provide the opportunity for enhanced combustion and/or engine control so that greater fuel economy and/or reduced emissions may be achieved.

For more information about forming electrodes and the MOS layers and temperature and oxygen level sensing, see U.S. Pat. Nos. 8,586,394; 9,291,526; and 9,625,352. The disclosures of any patents/applications disclosed herein are hereby incorporated herein by reference in their entirety.

The present disclosure may, of course, be carried out in other ways than those specifically set forth herein without departing from essential characteristics of the disclosure. The present embodiments are to be considered in all respects as illustrative and not restrictive, and all changes coming within the meaning and equivalency range of the appended claims are intended to be embraced therein.

What is claimed is:

1. A method of monitoring for a combustion misfire event in an internal combustion engine with continual periodic combustion events, the method comprising:
generating a first combustion signal indicative of an exhaust state of the engine based on a time-varying resistance of a first oxygen sensor disposed in an exhaust plenum of the engine; wherein the first oxygen sensor is a resistive-based oxygen sensor comprising:
a metal oxide semiconductor layer bridging a gap between first and second electrodes; and
a porous protective layer covering the metal oxide semiconductor layer;
generating a second combustion signal indicative of the exhaust state of the engine based on a second oxygen sensor disposed in the exhaust plenum proximate the first oxygen sensor; wherein the second oxygen sensor is a voltaic-based or ampometric-based oxygen sensor;
wherein the first oxygen sensor has a first response time for detecting a change in temperature and/or oxygen content of exhaust gases in the exhaust plenum that is at least twice as fast as a second response time of the second oxygen sensor for detecting the same change in temperature and/or oxygen content of exhaust gases in the exhaust plenum; and
monitoring for a combustion misfire event by comparing the first combustion signal and the second combustion signal.

2. The method of claim 1, wherein the second oxygen sensor is a voltaic-based narrowband oxygen sensor.

3. The method of claim 1, wherein the second oxygen sensor is an ampometric-based wideband oxygen sensor.

4. The method of claim 1, wherein the metal oxide semiconductor layer of the first oxygen sensor comprises a p-type metal oxide semiconductor material.

5. The method of claim 1, wherein the metal oxide semiconductor layer of the first oxygen sensor comprises an n-type metal oxide semiconductor material.

6. The method of claim 1, wherein the monitoring comprises determining that a combustion misfire event has occurred if a difference between the first combustion signal and the second combustion signal exceeds a first threshold.

7. The method of claim 1, wherein the monitoring comprises determining that a combustion misfire event has occurred if a difference between the first combustion signal and the second combustion signal exceeds a first threshold for at least a minimum duration.

8. The method of claim 7, further comprising changing the minimum duration in response to a change in speed of the internal combustion engine.

9. The method of claim 1, wherein the first and second oxygen sensors are co-located along the exhaust plenum.

10. The method of claim 1, wherein the first oxygen sensor and the second oxygen sensor are disposed in spaced relation to each other, with the first oxygen sensor disposed operatively upstream of the second oxygen sensor relative to the exhaust plenum.

11. A combustion misfire sensor assembly for monitoring for a combustion misfire in an internal combustion engine with continual periodic combustion events, the assembly comprising:
a first oxygen sensor configured to be disposed in an exhaust plenum of the engine; wherein the first oxygen sensor is a resistive-based oxygen sensor comprising:
a metal oxide semiconductor layer bridging a gap between first and second electrodes; and
a porous protective layer covering the metal oxide semiconductor layer;
a second oxygen sensor configured to be disposed in the exhaust plenum in proximity to the first oxygen sensor; wherein the second oxygen sensor is a voltaic-based or ampometric-based oxygen sensor;
processing circuitry operatively connected to the first and second oxygen sensors and configured to:
monitor for a combustion misfire by comparing a first combustion signal and a second combustion signal;
wherein the first combustion signal is derived from the first oxygen sensor and indicates an exhaust state of the engine based on a time-varying resistance of the first oxygen sensor;
wherein the second combustion signal is derived from the second oxygen sensor and indicates the exhaust state of the engine based on a time-varying response of the second oxygen sensor; and
wherein the first oxygen sensor has a first response time for detecting a change in temperature and/or oxygen content of exhaust gases in the exhaust plenum that is at least twice as fast as a second response time of the second oxygen sensor for detecting the same change in temperature and/or oxygen content of exhaust gases in the exhaust plenum.

12. The combustion misfire sensor assembly of claim 11, wherein the second oxygen sensor is a voltaic-based narrowband oxygen sensor.

13. The combustion misfire sensor assembly of claim 11, wherein the second oxygen sensor is an ampometric-based wideband oxygen sensor.

14. The combustion misfire sensor assembly of claim 11, wherein the metal oxide semiconductor layer of the first oxygen sensor comprises a p-type metal oxide semiconductor material.

15. The combustion misfire sensor assembly of claim 11, wherein the metal oxide semiconductor layer of the first oxygen sensor comprises an n-type metal oxide semiconductor material.

16. The combustion misfire sensor assembly of claim 11, wherein the processing circuitry is configured to determine that a combustion misfire event has occurred if a difference between the first combustion signal and the second combustion signal exceeds a first threshold.

17. The combustion misfire sensor assembly of claim 16, wherein the processing circuitry is configured to determine that a combustion misfire event has occurred if the difference between the first combustion signal and the second combustion signal exceeds the first threshold for at least a minimum duration.

18. The combustion misfire sensor assembly of claim 17, wherein the processing circuitry is configured to change the minimum duration in response to a change in speed of the combustion engine.

19. The combustion misfire sensor assembly of claim 11, wherein the combustion engine is an internal combustion engine for a vehicle.

20. The combustion misfire sensor assembly of claim 11, wherein the first oxygen sensor and the second oxygen sensor are disposed in spaced relation to each other, with the first oxygen sensor disposed upstream of the second oxygen sensor relative to the exhaust plenum.

* * * * *